(12) United States Patent  
Kawahara et al.

(10) Patent No.: US 6,647,090 B2  
(45) Date of Patent: Nov. 11, 2003

(54) X-RAY FLUORESCENCE SPECTROMETER

(75) Inventors: Naoki Kawahara, Takatsuki (JP); Kouichi Aoyagi, Takatsuki (JP); Yasujiro Yamada, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 10/126,697

(22) Filed: Apr. 22, 2002

(65) Prior Publication Data

US 2002/0172322 A1 Nov. 21, 2002

(30) Foreign Application Priority Data

May 15, 2001 (JP) .......................................... 2001-144176

(51) Int. Cl.⁷ ............................................ G01N 23/223
(52) U.S. Cl. ............................................ 378/45; 378/44
(58) Field of Search ............................. 378/45, 44, 46, 378/49, 50, 70, 80, 82, 86, 88

(56) References Cited

U.S. PATENT DOCUMENTS 5,280,513 A * 1/1994 Meltzer ........................ 378/90  
6,337,897 B1 * 1/2002 Kawahara et al. ............ 378/45  
6,389,102 B2 * 5/2002 Mazor et al. .................. 378/89  
6,442,231 B1 * 8/2002 O'Hara ......................... 378/45

* cited by examiner

Primary Examiner—Drew A. Dunn  
Assistant Examiner—Hoon Song  
(74) Attorney, Agent, or Firm—Birch, Stewart, Kolasch & Birch, LLP

(57) ABSTRACT

To provide an X-ray fluorescence spectrometer capable of providing a stable fluorescent X-ray intensity regardless of the presence of irregularities or the like on a surface of a sample to be analyzed, the X-ray fluorescence spectrometer includes an X-ray source 1 including a primary X-ray limiting diaphragm 3. An aperture 3a of the primary X-ray limiting diaphragm 3 is of a shape effective to allow change in intensity of fluorescent X-rays 7 measured by a detector 8 to be not higher than 1% in the event that a height of the sample surface 5a relative to the X-ray source 1 and the detector 8 changes 1 mm at maximum.

5 Claims, 3 Drawing Sheets

X-RAY FLUORESCENCE SPECTROMETER

BACKGROUND OF THE INVENTION

1. Field of the Invention

The present invention relates to an X-ray fluorescence spectrometer having an optical system by so-called parallel beam method.

2. Description of the Prior Art

In the X-ray fluorescence analysis, for example, a sample is in the form of a disc of a predetermined size, after having been retained by a predetermined sample holder, placed on a sample support table and is then irradiated by primary X-rays emitted from an X-ray source such as an X-ray tube so as to impinge upon a surface of such sample. In general, in order to increase the sensitivity of the spectrometer, the X-ray source is positioned as close to the sample as possible. Considering, however, that it is at the same time necessary for the X-ray source not to disturb and interfere the field of view of the detecting means aimed at the sample surface, the X-ray source such as the X-ray tube is generally disposed slantwise relative to the sample surface.

However, it has been found that if the distance between the X-ray source and the sample surface is chosen to be very small, slight change of such distance as a result of the presence of irregularities, warps or deflections up to about 1 mm on the sample surface brings about an unnegligible change in intensity of the fluorescent X-rays emitted from the sample, resulting in insufficient improvement over the analyzing accuracy.

SUMMARY OF THE INVENTION

Accordingly, the present invention has been devised to substantially eliminate the inconveniences inherent in the prior art X-ray fluorescence spectrometer and is intended to provide an improved X-ray fluorescence spectrometer capable of providing a stable fluorescent X-ray intensity.

In order to accomplish the foregoing object, the present invention provides an X-ray fluorescence spectrometer which includes a sample support table for supporting thereon a sample to be analyzed, an X-ray source for radiating primary X-rays so as to impinge slantwise on a flat surface of the sample and including a primary X-ray limiting diaphragm having an aperture for limiting a bundle of the primary X-rays emitted therefrom towards the sample surface, and a detecting means positioned so as to aim slantwise at the sample surface for measuring an intensity of fluorescent X-rays emitted from a site of interest of the sample. The detecting means includes a field limiting diaphragm having an aperture for limiting a field of view encompassing the sample surface and a soller slit for collimating the fluorescent X-rays emitted from the sample. The aperture of the primary X-ray limiting diaphragm is of a shape effective to allow change in intensity of the fluorescent X-rays measured by the detecting means to be not higher than 1% in the event that a height of the sample surface relative to the X-ray source and the detecting means changes 1 mm at maximum.

According to the present invention, since the aperture of the primary X-ray limiting diaphragm is of a shape uniquely designed as to allow change in intensity of the fluorescent X-rays measured by the detecting means to be not higher than 1% in the event that a height of the sample surface relative to the X-ray source and the detecting means changes 1 mm at maximum, the stable fluorescent X-ray intensity can be secured regardless of the presence of the irregularities or the like on the sample surface and, accordingly, the analyzing accuracy can be sufficiently increased.

Also, a similar effect can be equally obtained even if the respective apertures of the primary X-ray limiting diaphragm and the field limiting diaphragm are uniquely designed and shaped.

For example, the aperture of the primary X-ray limiting diaphragm may be of a substantially round shape with a portion thereof blocked, the aperture of the field limiting diaphragm may be of a substantially oval shape with a portion thereof blocked.

Preferably a rotary mechanism is employed to rotate the sample.

BRIEF DESCRIPTION OF THE DRAWINGS

In any event, the present invention will become more clearly understood from the following description of a preferred embodiment thereof, when taken in conjunction with the accompanying drawings. However, the embodiment and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENT

Figure 1:
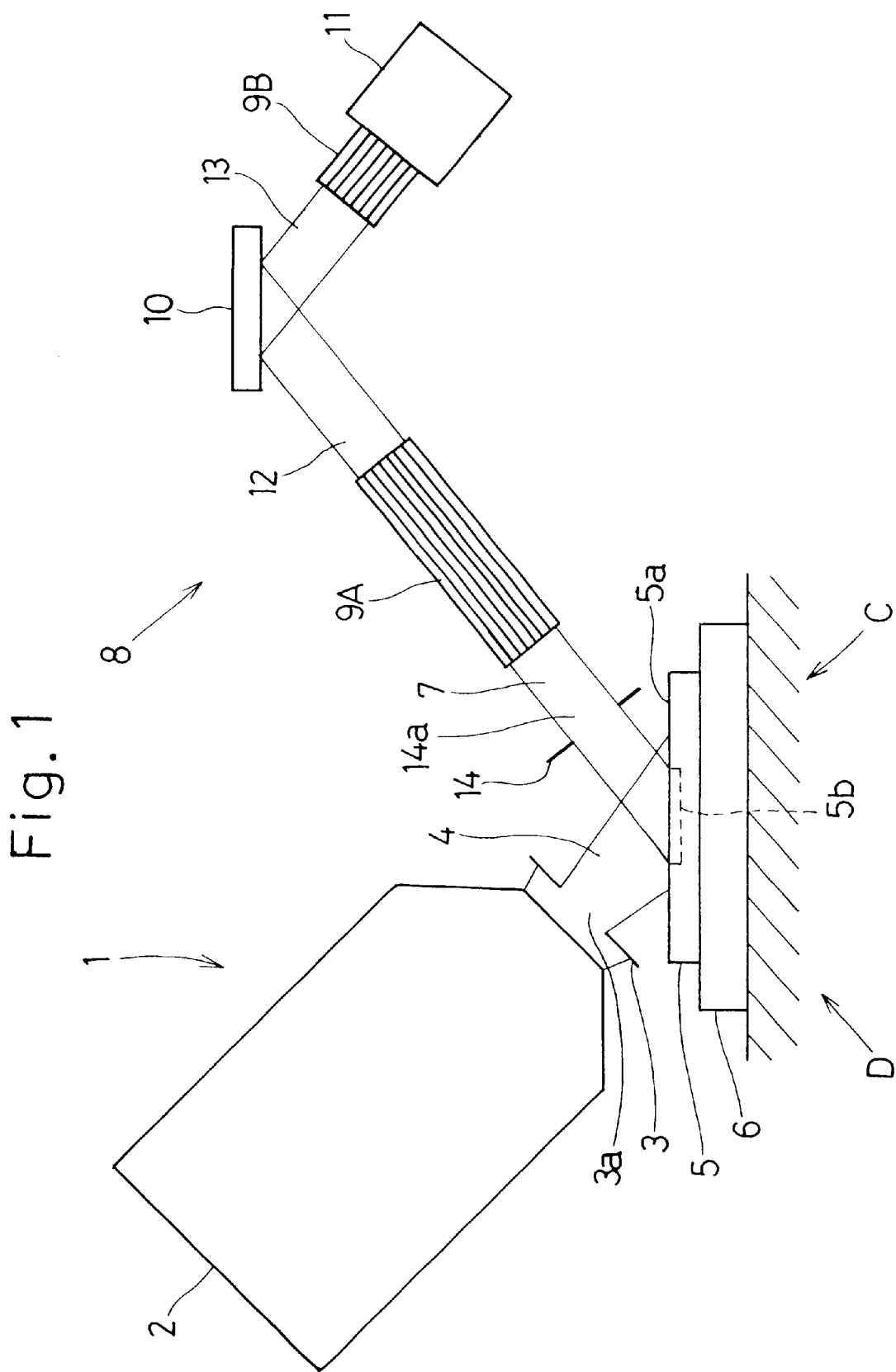
FIG. 1 is a schematic diagram showing an X-ray fluorescence spectrometer embodying the present invention.

Hereinafter, an X-ray fluorescence spectrometer according to a preferred embodiment of the present invention will be described. As shown in FIG. 1, the X-ray fluorescence spectrometer includes a sample support table 6 on which a sample 5 to be analyzed is placed, an X-ray source 1 for radiating primary X-rays 4 so as to impinge on a flat surface 5a of the sample 5, and a detecting means 8 positioned so as to aim at the sample surface 5a for measuring the intensity of fluorescent X-rays 7 emitted from a site of interest 5b of the sample 5. The sample 5 may be in the form of, for example, a disc of a predetermined size. Although the sample 5 is placed direct on the sample support table 6, the sample 5 may be placed on the sample support table 6 through a predetermined sample holder which may be designed to hold the sample. During the measurement, the sample support table 6 is driven by a motor-driven rotary mechanism 16 so as to rotate about a center axis of the sample 5 which may lie perpendicular to the sample support table 6. It is to be noted that the flat surface 5a of the sample 5 may have surface irregularities, warps, deflections or the like up to about 1 mm.

The detecting means 8 includes a field limiting diaphragm 14 for limiting the field of view encompassing the sample surface 5a, a divergence soller slit 9A for passing therethrough the fluorescent X-rays emitted from the sample 5, a spectroscopic device 10 for receiving the fluorescent X-rays that have passed through the divergence soller slit 9A and which is operable to diffracting fluorescent X-rays 13 of a wavelength to be analyzed, a light-intercepting soller slit 9B for passing therethrough the fluorescent X-rays 13 that have been diffracted by the spectroscopic device 10, and a detector 11 for measuring the intensity of the fluorescent X-rays that have passed through the light-intercepting soller slit 9B. The field limiting diaphragm 14 is utilized to limit the fluorescent X-rays emitted from the sample 5 so that only a fluorescent X-ray 7 emanating from the site of interest 5b of the sample 5 can impinge upon the detector 11. The divergence soller slit 9A is so disposed as to incline relative to the sample surface 5a, with its opening oriented so as to aim at that portion of the sample surface 5a that is encompassed by the field limiting diaphragm 14 while the site of interest 5b of the sample 5 includes that portion of the sample surface 5a and a depthwise region of the sample 5 aligned with that portion of the sample surface 5a. It is to be noted that the divergence soller slit 9A and the light-intercepting soller slit 9B cooperate with each other to define a soller slit 9 operable to collimate the fluorescent X-rays emitted from the sample 5.

The X-ray source 1 includes an X-ray tube 2 and a primary X-ray limiting diaphragm 3 for limiting a bundle of the primary X-rays 4 emitted therefrom towards the sample surface 5a and is disposed on one side opposite to the detecting means 8 with respect to the center position of the sample surface 5a. Since the X-ray source 1 is disposed as near the sample surface 5a as possible while the detecting means 8 is so disposed as to aim at and encompass the sample surface 5a, and since the direction in which the primary X-rays 4 travel from the X-ray source 1 is inclined relative to the sample surface 5a, the radiating intensity of the primary X-rays 4 emitted from the X-ray source 1 and impinging upon the sample surface 5a as viewed from front of the sheet of FIG. 1 is distributed not to represent a symmetrical hill-shaped pattern, but to represent a pattern in which a peak is biased in a direction counter to the detecting means 8 (i.e., leftwards as viewed in FIG. 2) as shown by A in FIG. 2.

Figure 2:
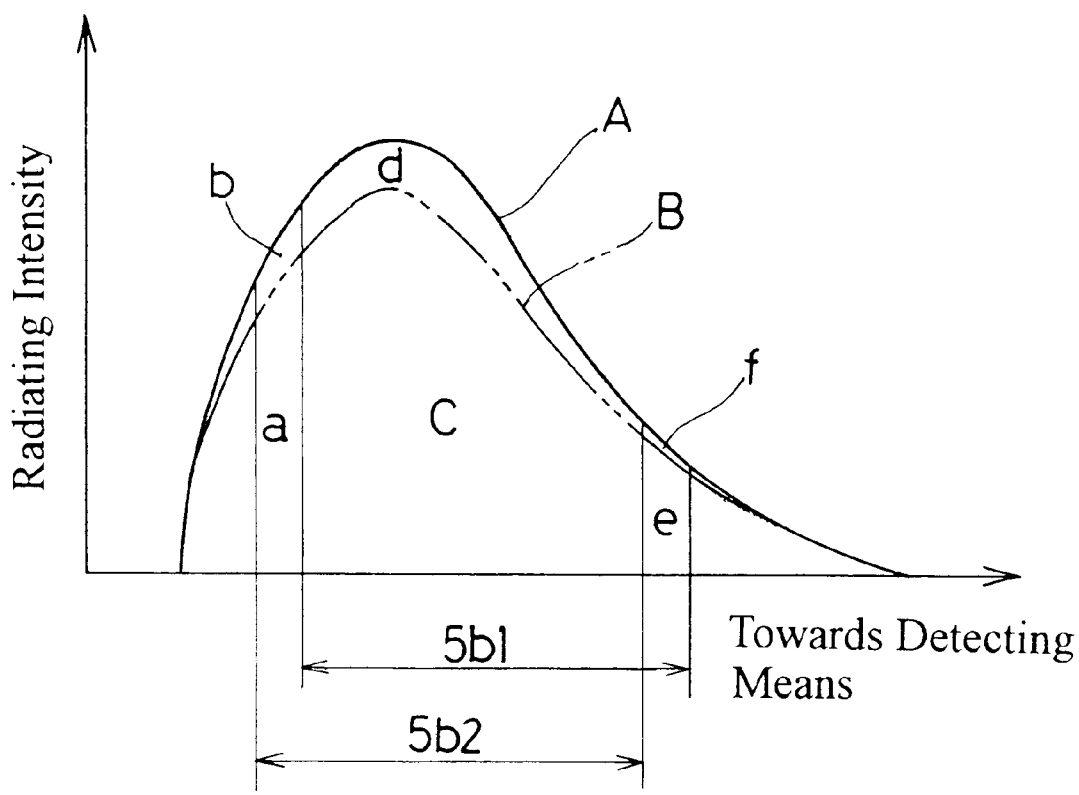
FIG. 2 is a schematic diagram showing patterns of distribution of radiating intensities of primary X-rays emitted from an X-ray source towards a sample surface as viewed from front of the sheet of FIG. 1.

Assuming that in FIG. 1 the height of the sample surface 5a relative to the X-ray source 1 and the detecting means 8 changes, for example, descends 1 mm with the sample surface 5a consequently moved a corresponding distance away from the X-ray source 1, the radiating intensity of the primary X-rays 4 impinging upon the sample surface 5a is a little lowered all over in its distribution as shown by B in FIG. 2. At the same time, since as shown in FIG. 1 the detecting means 8 positioned on one side opposite to the X-ray source 1 'looks' slantwise at the sample surface 5a, the position of the site of interest 5b on the sample surface 5a displaces leftwards as viewed in FIG. 1, that is, from a position 5b1 towards a position 5b2 as shown in FIG. 2. Accordingly, the radiating intensity of the primary X-rays 4 impinging upon the site of interest 5b of the sample 5 changes from (c+d+e+f=I1) to (a+c=I2) when expressed in terms of areas shown in FIG. 2.

So long as the change from I1 to I2 expressed by (|I2−I1|×100/I1) is not higher than 1%, the intensity of the fluorescent X-rays generated may also be stabilized. However, the prior art has not been so devised and is susceptible to change (and in most cases, lowering) over a few percentages. The inventor(s) of the present invention has (have) found that the reason therefore is because, where the design has been made to merely position the X-ray source at a location as near the sample as possible, the quantity d of the radiating intensity that is reduced as a result of the sample surface having been moved away from the X-ray source tends to be greater than the quantity a−(e+f) of the radiating intensity that is increased as a result of the sample surface having been so moved.

Figure 3:
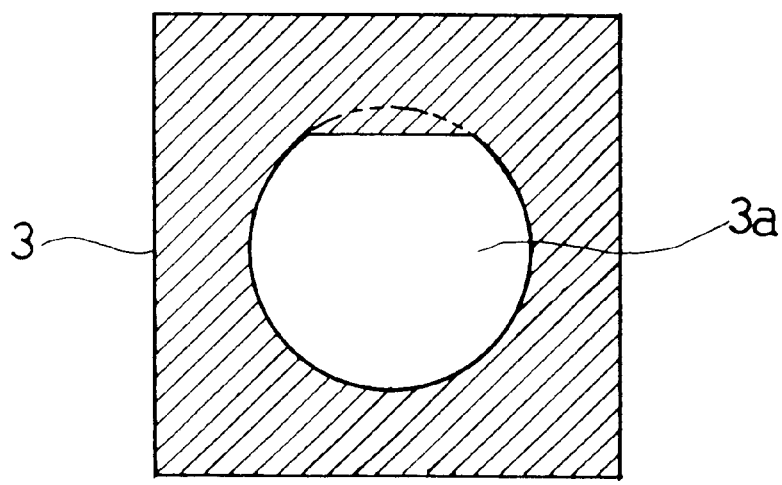
FIG. 3 is a schematic diagram showing a primary X-ray limiting diaphragm employed in the X-ray fluorescence spectrometer as viewed in a direction conforming to the direction in which the primary X-rays are emitted.

In view of the foregoing, the spectrometer embodying the present invention is so devised that while the sample support table 1, the X-ray tube 2 and the detecting means 8 are left unchanged in their positional relation, that is, so positioned relative to each other as shown in FIG. 1, the primary X-ray limiting diaphragm 3 for limiting the bundle of the primary X-rays 4 used to irradiate the sample surface 5a is positioned in front of an emission port of the X-ray tube 2, as a part of the X-ray source 1. The primary X-ray limiting diaphragm 3 has an aperture 3a of a shape designed as shown in FIG. 3, when viewed in a direction conforming to the direction of irradiation of the primary X-rays 4 (i.e., as viewed in a direction shown by the arrow C in FIG. 1), so that in the event that the height of the sample surface 5a relative to the X-ray source 1 and the detecting means 8 changes 1 mm at maximum, the change of the intensity of the fluorescent X-rays 7 measured by the detecting means 8 may not be higher than 1%. In other words, as shown in FIG. 3, the aperture 3a of the primary X-ray limiting diaphragm 3 does not represent a mere round shape, but represents such a round shape in which a portion of the circle closest to the detecting means 8 (an upper region as shown in FIG. 3) is blocked or closed. Although so far shown in FIG. 3, the chord joining two points on a curve represented by the shape of the aperture 3a is shown as extending straight, it is to be noted that the chord may take any desired shape different from the straight line segment. It is also to be noted that a basic shape of the aperture 3a of the primary X-ray limiting diaphragm 3 prior to being blocked in the manner described above, may not be limited to a round shape as shown, but may represent an oval shape or a polygonal shape. It is again to be noted that in FIG. 3, as well as FIG. 4 as will be subsequently referred to, a portion of the primary X-ray limiting diaphragm 3 other than the aperture 3a is shown as hatched.

According to the above described structure, referring to the patterns A and B of the radiating intensities shown in FIG. 2, a portion of the radiating intensity pattern adjacent (rightwards) the detecting means 8 is lower than that exhibited by the prior art and, hence, the area (e+f) becomes smaller. Accordingly, the quantity a−(e+f) of the radiating intensity that is increased as a result of the site of interest 5b of the sample surface 5 having been so moved is greater than, that exhibited by the prior art and can be substantially counterbalanced with the quantity d of the radiating intensity that is reduced as a result of the sample surface 5a having been moved away from the X-ray source 1. By way of example, assuming that the height of the sample surface 5a relative to the X-ray source 1 and the detecting means 8 changes 1 mm, change in intensity of the fluorescent X-rays 7 measured by the detecting means 8 has been found 0.6% when the primary X-ray limiting diaphragm 3 shown in FIG. 3 is employed, in contrast to 6% exhibited when a similar primary X-ray limiting diaphragm of a mere round shape is employed. Thus, with the X-ray fluorescence spectrometer embodying the present invention, the stable fluorescent X-ray intensity can be secured notwithstanding the presence of irregularities or the like on the sample surface 5a.

Figure 4:
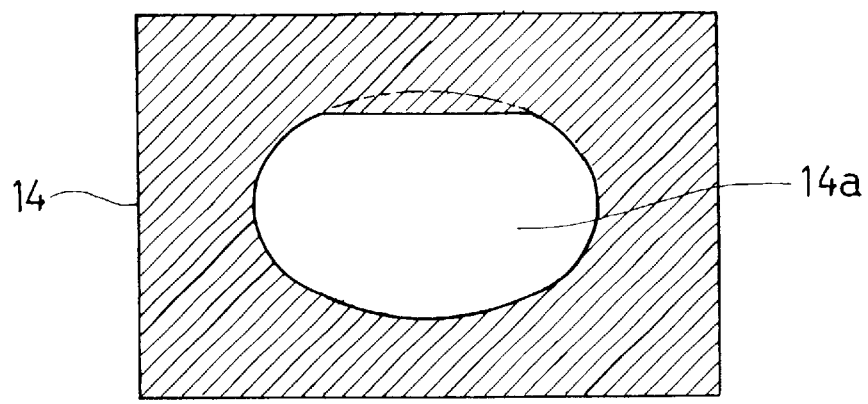
FIG. 4 is a schematic diagram showing a field limiting diaphragm employed in the X-ray fluorescence spectrometer as viewed in a direction conforming to the direction in which fluorescent X-rays enter a detecting means.

An effect similar to that described above can be equally obtained even if respective shapes of the aperture 3a of the primary X-ray limiting diaphragm 3 and an aperture 14a of the field limiting diaphragm 14 are adjusted. More specifically, while the aperture 14a of the field limiting aperture 14 is generally of an oval shape (as will be described in detail later) so that an upper surface of the site of interest 5b of the sample surface 5a which is round in shape can be sufficiently encompassed thereby, the aperture 14a may be of a shape in which a portion of the substantially oval shape closest to the X-ray source 1 (an upper region as shown in FIG. 4) is blocked or closed as shown in FIG. 4 which illustrates the shape of the aperture 14a as viewed in a direction shown by the arrow D in FIG. 1. In this example, the chord joining two points on a curve represented by the shape of the aperture 14a is shown as extending straight, it is to be noted that the chord may take any desired shape different from the straight line segment. In such case, in addition to the advantages brought about by the use of the unique geometric shape of the aperture 3a of the primary X-ray limiting diaphragm 3 discussed above, there is an additional advantage that since a left side of sites of interest 5b1 and 5b2 can be shifted rightwards as compared with that according to the prior art to thereby reduce d and increase a as compared with those according to the prior art, the quantity a−(e+f) of the radiating intensity that is increased as a result of the site of interest 5b of the sample surface 5 having been so moved and the quantity d of the radiating intensity that is reduced as a result of the sample surface 5a having been moved away from the X-ray source 1 can be substantially counterbalanced with each other.

It is to be noted that in the system shown in FIG. 1, to avoid the primary X-rays 4 entering directly the detecting means 8, the aperture 14a of the field limiting diaphragm 14 may be partially blocked, that is, the aperture 14a may be of a shape in which that portion of the substantially oval shape is blocked as shown in FIG. 4. However, even in this case, the shape of the aperture 14a of the field limiting diaphragm 14 has to be again designed, provided that the aperture 3a of the primary X-ray limiting diaphragm 3a and the aperture 14a of the field limiting diaphragm 14 are so shaped and so configured as to attain the effects brought about by the present invention. By way of example, the position (height) of the chord of that portion blocking the substantially oval shape of the aperture 14a has to be readjusted. Also, it appears that a portion of the round upper surface of the site of interest 5b on the sample surface 5a may not be encompassed by the detecting means 8 if the aperture 14a of the field limiting diaphragm 14 is chosen to represent the shape in which that portion of the substantially oval shape is blocked, but the reality is that since during the measurement the disc-shaped sample 5 is rotated about the center axis thereof by the motor-driven rotary mechanism 16 as hereinbefore described to avoid the problem associated with unevenness of the sample 5, the fluorescent X-rays 7 emanating from the site of interest 5b can be sufficiently sensed by the detecting means 8.

Figure 5:
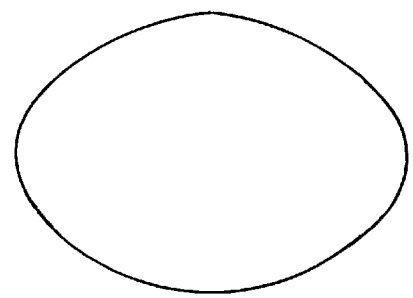
FIG. 5 is a schematic diagram showing one example of a basic shape of an aperture of the field limiting diaphragm.
Figure 6:
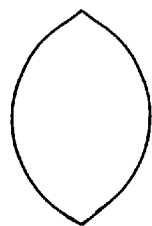
FIG. 6 is a schematic diagram showing another example of the basic shape of the aperture of the field limiting diaphragm.

In the foregoing description, the term "substantially oval" has been used in connection with the basic shape of the aperture 14a of the field limiting diaphragm 14 prior to that portion thereof being blocked. The reason therefore will now be discussed. Since the distance from any point on the field limiting diaphragm 14 to the sample surface 5a is not fixed, the basic shape of the aperture 14a does not represent a strictly oval shape in order for the upper surface of the round site of interest 5b of the sample surface 5a to be sufficiently encompassed by the field of view of the detecting means 8, that is, in order for the fluorescent X-rays 7 emanating from the site of interest 5b to be detected in its entirety by the detecting means 8 with no external rays being mixed into such fluorescent X-rays 7, and will represent such a quasi-oval shape wherein as shown in FIG. 5 a lower region of the round shape is constricted and an upper region of the round shape is constricted more than the lower region thereof. Where the site of interest 5b is small, it may represent a generally longitudinally elongated shape as shown in FIG. 6. Also, it may occur that the upper surface of the site of interest 5b may represent any other shape than the round shape on the sample surface 5a. Accordingly, the basic shape of the aperture 14a of the field limiting diaphragm 14 prior to that portion thereof being blocked is to be understood as including a substantially round shape, a substantially oval shape and a substantially polygonal shape.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A X-ray fluorescence spectrometer which comprises:
   a sample support table for supporting thereon a sample to be analyzed;
   an X-ray source for radiating primary X-rays so as to impinge slantwise on a flat surface of the sample and including a primary X-ray limiting diaphragm for limiting a bundle of the primary X-rays emitted therefrom towards the sample surface, said primary X-ray limiting diaphragm having an aperture; and
   a detecting means positioned so as to aim slantwise at the sample surface for measuring an intensity of fluorescent X-rays emitted from a site of interest of the sample, said detecting means including a field limiting diaphragm for limiting a field of view encompassing the sample surface and a soller slit for collimating the fluorescent X-rays emitted from the sample, said field limiting diaphragm having an aperture;
   wherein the aperture of the primary X-ray limiting diaphragm is of a shape effective to allow change in intensity of the fluorescent X-rays measured by the detecting means to be not higher than 1% in the event that a height of the sample surface relative to the X-ray source and the detecting means changes 1 mm at maximum.

2. The X-ray fluorescence spectrometer as claimed in claim 1, wherein the respective apertures of the primary X-ray limiting diaphragm and the field limiting diaphragm are of a shape effective to allow change in intensity of the fluorescent X-rays measured by the detecting means to be not higher than 1% in the event that a height of the sample surface relative to the X-ray source and the detecting means changes 1 mm at maximum.

3. The X-ray fluorescence spectrometer as claimed in claim 1, wherein the aperture of the primary X-ray limiting diaphragm is of a substantially round shape with a portion thereof blocked.

4. The X-ray fluorescence spectrometer as claimed in claim 2, wherein the aperture of the field limiting diaphragm is of a substantially oval shape with a portion thereof blocked.

5. The X-ray fluorescence spectrometer as claimed in claim 1, further comprising a rotary mechanism for rotating the sample.

* * * * *